United States Patent
Knauf et al.

(10) Patent No.: US 10,875,827 B2
(45) Date of Patent: Dec. 29, 2020

(54) PROCESS FOR PREPARING AN ISOCYANATE BY PARTLY ADIABATIC PHOSGENATION OF THE CORRESPONDING AMINE

(71) Applicant: Covestro Deutschland AG, Leverkusen (DE)

(72) Inventors: Thomas Knauf, Dormagen (DE); Juergen Spriewald, Kölln-Reisiek (DE); Anke Hielscher, Cologne (DE); Volker Michele, Cologne (DE); Dietmar Wastian, Dormagen (DE); Christian Steffens, Cologne (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/677,752

(22) Filed: Nov. 8, 2019

(65) Prior Publication Data

US 2020/0148630 A1    May 14, 2020

(30) Foreign Application Priority Data

Nov. 13, 2018 (EP) .................................... 18205953

(51) Int. Cl.
   *C07C 263/10*    (2006.01)
(52) U.S. Cl.
   CPC .................................. *C07C 263/10* (2013.01)
(58) Field of Classification Search
   CPC .................................................. C07C 263/10
   See application file for complete search history.

(56) References Cited

U.S. PATENT DOCUMENTS

| | | | |
|---|---|---|---|
| 4,581,174 A | 4/1986 | Ohlinger et al. | |
| 5,931,579 A | 8/1999 | Gallus et al. | |
| 7,112,694 B2 | 9/2006 | Woelfert et al. | |
| 7,851,648 B2 * | 12/2010 | Sohn .................... | C07C 263/10 560/347 |
| 8,079,752 B2 | 12/2011 | Rausch et al. | |
| 8,097,751 B2 | 1/2012 | Koch et al. | |
| 2007/0265465 A1 | 11/2007 | Keggenhoff et al. | |
| 2018/0186729 A1 | 7/2018 | Busch et al. | |

FOREIGN PATENT DOCUMENTS

| | | |
|---|---|---|
| EP | 1873142 A1 | 1/2008 |
| GB | 1173890 | 12/1969 |

* cited by examiner

*Primary Examiner* — Paul A Zucker
(74) *Attorney, Agent, or Firm* — Donald R. Palladino

(57) ABSTRACT

The present invention relates to a process for preparing an isocyanate by reacting a primary amine with phosgene, comprising I) providing an amine solution, II) providing a phosgene solution, III) mixing the amine solution with the phosgene solution in a mixing unit, followed by IV) further conversion in an adiabatically operated reaction zone and the removing of the gas phase formed as a result of the chemical reaction in a separation zone, V) expanding the remaining liquid phase in two or three stages, VI) further conversion of the liquid phase remaining after the last expansion stage in an indirectly heated reaction zone and VII) isolating the isocyanate from the reaction solution obtained therein.

16 Claims, No Drawings

PROCESS FOR PREPARING AN ISOCYANATE BY PARTLY ADIABATIC PHOSGENATION OF THE CORRESPONDING AMINE

CROSS-REFERENCE TO RELATED APPLICATION

This application claims priority to European Application No. 18205953.5, filed Nov. 13, 2018, which is incorporated herein by reference.

FIELD

The present invention relates to a process for preparing an isocyanate by reacting a primary amine with phosgene, comprising I) providing an amine solution, II) providing a phosgene solution, III) mixing the amine solution with the phosgene solution in a mixing unit, followed by IV) further conversion in an adiabatically operated reaction zone and the removing of the gas phase formed as a result of the chemical reaction in a separation zone, V) expanding the remaining liquid phase in two to three stages, VI) further conversion of the liquid phase remaining after the last expansion stage in an indirectly heated reaction zone and VII) isolating the isocyanate from the reaction solution obtained therein.

BACKGROUND

Isocyanates (1) are prepared in large volumes and serve mainly as starting materials for production of polyurethanes. They are usually prepared by reacting the corresponding amines (2) with phosgene (3), using phosgene in a stoichiometric excess. The reaction of the amines with the phosgene can be effected either in the gas phase or in the liquid phase, wherein the reaction can be conducted batchwise or continuously. The phosgenation reaction—in the case of gas phase phosgenation after the quench of the gaseous reaction product obtained at first—gives a liquid phase comprising the desired isocyanate. As well as this liquid phase, gas streams are obtained at various points in the process, which, once they have been freed of products of value such as hydrogen chloride, phosgene, isocyanate and solvent as far as technically possible and economically viable, are generally sent to a phosgene breakdown in which trace fractions of phosgene that have not been removed in the preceding workup steps are broken down catalytically with water. In general, activated carbon is used as catalyst for the purpose. This phosgene breakdown gives a cleaned off gas and an acidic wastewater stream that has to be disposed of. This wastewater stream generally still contains organic impurities, for example solvent (typically monochlorobenzene in the case of preparation of MDI), amine (aniline in the case of preparation of MDI) and urea compounds. These organic impurities must be very substantially removed before wastewater can be sent to a wastewater treatment plant (for example a biological sewage plant). One way of achieving this is to bring the wastewater to a pH>7, especially in the range from 11 to 13, by addition of base (for example sodium hydroxide solution) and then to adsorb the organic impurities on activated carbon. Such an adsorption on activated carbon enables, in a simple manner, the reduction of the concentration of organic impurities in this wastewater stream to a level that allows the wastewater to be sent to a wastewater treatment plant.

Processes for preparing organic isocyanates from primary amines and phosgene have already been described many times before; merely by way of example, reference is made to the following documents:

DE-A-34 03 204 describes a continuous process for preparing organic polyisocyanates, in which elevated temperatures of 100 to 220° C. are established in a reaction involving partial circulation at a pressure of 5 to 100 bar.

DE-A-17 68 439 describes a process for continuously preparing organic isocyanates, in which the amine and phosgene feedstocks are first preheated and then the preheated constituents are combined in the reaction zone under high pressures and reacted under isothermal conditions, i.e. under heat exchange with the environment.

DE-A-102 22 968 describes a process for continuously preparing polyisocyanates by reacting primary amines with phosgene, in which the reaction is conducted in a cascade of temperature-adjustable reaction tubes of different size.

EP 1 873 142 A1 describes a three-stage process regime in which the pressure between the first stage of a mixer and the second stage of a first phosgenation reactor remains the same or rises and, in the third stage, an apparatus for phosgene removal, the pressure is lower than in the second stage. The reaction can be run adiabatically or isothermally.

Of interest on the industrial scale are both aromatic isocyanates, such as methylene diphenylene diisocyanate (MMDI henceforth—"monomeric MDI"), mixtures of MMDI and polymethylene polyphenylene polyisocyanates (i.e. the higher homologues of MMDI, PMDI henceforth, "polymeric MDI") or tolylene diisocyanate (TDI), and aliphatic isocyanates, for example pentane 1,5-diisocyanate (PDI), hexamethylene 1,6-diisocyanate (HDI) or isophorone diisocyanate (IPDI). In addition, isocyanates having benzylic isocyanate groups are also important; particular mention should be made here of xylylene diisocyanate (XDI). The present invention is especially concerned with the preparation of methylene diphenylene diisocyanates and polymethylene polyphenylene polyisocyanates (collectively called MDI henceforth).

In the majority of the known processes, the desired reaction temperature is established using temperature-controllable reactors in different variants (jacket heating, heating by heat exchangers or special reactor internals). In the isocyanate synthesis by phosgenation of amines, however, the external control of the temperature of the reactors often constitutes a problem since the high temperatures of the reactor wall surfaces promote or even actually cause the formation of by-products, which then adversely affect the yield and/or product properties. Moreover, deposits are then formed in the reactor, which necessitate regular shutdown and cleaning of the reactors. But this leads to a loss of plant capacity and hence to an economic disadvantage. Furthermore, the heat carrier systems incur additional capital costs, which likewise worsens the economic viability of the process. To solve these problems, EP 1 616 857 A1 proposes a two-stage process regime in which in a first stage a) amine and phosgene are reacted in an adiabatic reaction, where the reaction temperature is limited to values between 100 and 220° C. by setting the absolute pressure in the reactor specifically to values between 8 and 50 bar by expansion, and keeping the temperature at values between 100 and 220° C. until a conversion of phosgene of at least 80% has been attained, and then in a second stage b) expanding the reaction mixture from the first stage to absolute pressures in the range from 1 to 15 bar and continuing conversion at temperatures between 90 and 240° C., typically with supply of heat. Such a process regime can be referred to as an adiabatic-isothermal process regime. What is essential to the process described is the setting of the reaction temperature in the adiabatically operated reactor (100° C. to 220° C., preferably 115° C. to 180° C., more preferably 120° C. to 150° C.) via the pressure in this reactor. This setting via the pressure is effected via controlled expansion by means of opening valves mounted on the reactor, with escape of portions of the reaction mixture from the reactor (see paragraph [0016]). There is no disclosure of setting of the temperature in the adiabatically operated reactor via targeted closed-loop control of reactant temperatures in EP 1 616 857 A1. The reaction mixture that leaves the adiabatically operated reactor is converted further in a second stage under isothermal conditions and expanded to a pressure below that in the first stage (cf. paragraph [0019]). At the outlet of the isothermally operated reactor, a gas phase and a liquid phase containing the isocyanate are withdrawn separately therefrom.

International patent application WO 2017/001320 A1 is concerned with a process for efficient provision of the hydrogen chloride obtained as coproduct in the phosgenation of amines for subsequent applications (for example a Deacon process). In this process, the crude product from the phosgenation (i.e. the process product obtained after maximum progression of the reaction), optionally after removal of a purge stream containing predominantly hydrogen chloride, still during the phosgenation itself, is expanded in one or more stages to a pressure $p_E$ greater than the pressure $p_F$ required for the subsequent application, and the remaining liquid phase containing the desired isocyanate is subjected to a dephosgenation known per se. The phosgene- and hydrogen chloride-containing gas stream obtained in the dephosgenation has a pressure lower than the pressure required for the subsequent application. This latter gas stream is therefore compressed, combined with the gas stream obtained in the dephosgenation and then subjected to an HCl-phosgene separation known per se, which results in a clean hydrogen chloride stream under such a pressure that it can be supplied to the intended subsequent application without compression (cf. FIG. 1 and the corresponding elucidations in the description). The advantage of this procedure is that a considerable portion of the hydrogen chloride obtained overall, namely the portion obtained in the single-stage or multistage expansion of the crude product, can be sent without compression to the HCl-phosgene separation and the subsequent application, which enables the building of smaller compressors. The process is based ultimately on conducting the reaction at comparatively high pressures, which enables conducting the expansion of the crude product from the phosgenation to a still comparatively high pressure level. The expansion is especially effected proceeding from pressures in the reaction in the range from 6.00 bar to 60.0 bar to pressures of the hydrogen chloride-containing gas phase withdrawn from the expansion in the range from 5.00 bar to 30.0 bar, preferably proceeding from pressures in the reaction in the range from 12.0 bar to 45.0 bar to pressures of the hydrogen chloride-containing gas phase withdrawn from the expansion in the range from 9.00 bar to 18.0 bar. In the case of a multistage expansion, the document discloses the use of a cascade of multiple separators connected in series with a successively falling pressure level, with combination of the gas phases obtained in each of the successive compressors to give the gas stream having the pressure $p_E$, which apparently means that all gas phases are expanded to the pressure of the gas phase obtained in the last separator.

The reaction of the amine with phosgene upstream of the single-stage or multistage expansion, according to the teaching of WO 2017/001320 A1, can also be conducted in a sequence of an adiabatically operated and isothermally operated reactor as described in EP 1 616 857 A1. Considering that the pressure in the isothermal stage of the process according to EP 1 616 857 A1 can still be up to 15 bar, this is understandable. Combination of the teaching of WO 2017/001320 A1 with the teaching of EP 1 616 857 A1 would therefore lead the person skilled in the art to employ the process described in WO 2017/001320 A1 downstream of the isothermal stage described in EP 1 616 857 A1 (i.e. after maximum progression of the reaction). A sequence of (a) adiabatic reaction regime, (b) separation of gas phase and liquid phase formed therein, (c) multistage expansion of the liquid phase separated off and (d) further reaction thereof under isothermal conditions is therefore not disclosed in application WO 2017/001320 A1.

The quality of a process for preparing isocyanates is firstly defined by the content of unwanted by-products in the product of the process. Secondly, the quality of a process is defined in that the whole operation of startup and production in regular operation until the shutdown of the process can be executed without technical production outage and without problems that would necessitate intervention in the operation, and that there are no losses of feedstocks, intermediates or end product.

Ideally, therefore, the industrial scale plants for performance of such preparation processes are designed such that the processes run in a robust manner in the event of appropriate quality of the auxiliaries and feedstocks used and correct choice of process parameters such as pressure, temperature, ratios of amount and concentrations of the auxiliaries and feedstocks, etc. This means that, in such continuously operated large-scale plants, there will ideally be no problems such as the formation of precipitates, which can settle out in plant components and, for example, block pipelines. On the other hand, optimal exploitation of the space-time yield also contributes to a not inconsiderable degree to an improvement in productivity and hence the economic viability of industrial scale phosgenation plants. If the production rate enters the limiting ranges of what is still possible in a given plant, the process parameters must then be run within a very narrow window in order that there are none of the problems outlined above with precipitates, caking and product quality.

In the two-stage adiabatic-isothermal process regime with distinctly different pressures in each stage which is known in principle (see EP 1 616 857 A1; see the examples of this application: 22 bar in the first stage and 2 bar in the second stage), the lowering of pressure downstream of the adiabatically operated stage can lead to foaming of the reaction solution, under some circumstances with formation of solids. Moreover, under all operating conditions, the functionality of the control system (maintenance of gas and liquid pressure) in the pressure-lowering step has to be assured. Finally, sufficient dwell time should be provided to ensure the clean separation of the gas phase formed when the pressure is lowered from the remaining liquid phase without causing excessive apparatus dimensions (and hence capital costs in particular).

SUMMARY

In summary, it can therefore be stated that, in a two-stage adiabatic-isothermal process regime with distinctly different pressures in the two stages, the step of lowering the pressure is not without challenges from the point of view of chemical energy and process control and with regard to maximum economic viability of the process, and there was still a need for improvement here over the prior art.

Taking account of this need, the present invention provides a process for preparing an isocyanate by reacting a primary amine with phosgene, comprising the steps of:

I) providing a solution of the primary amine in a solvent;

II) providing a solution of phosgene in a solvent;

III) mixing the solution of the primary amine provided in step I) and the solution of phosgene provided in step II) in a mixing unit to give a reaction mixture of a temperature in the range from 110° C. to 145° C. with observance of a stoichiometric excess of phosgene based on the amino groups of the primary amine in the range from 40% to 200% of theory, preferably in the range from 40% to 120% of theory, more preferably in the range from 50% to 100% of theory, most preferably in the range from 50% to 75% of theory;

IV) running the liquid reaction mixture obtained in step III) through a reaction zone and through a separation zone downstream in flow direction of this reaction zone to form a gas phase under a pressure in the range from 8.0 bar$_{(abs.)}$ to 50.0 bar$_{(abs.)}$, especially in the range from 15.0 bar$_{(abs.)}$ to 30.0 bar$_{(abs.)}$, from the liquid reaction mixture in the separation zone, where the reaction zone and the separation zone are not heated and not cooled, where the gas phase formed in the separation zone and the remaining liquid phase from the separation zone are removed separately from one another;

V) expanding the liquid phase withdrawn from the separation zone from step IV) with partial conversion of this liquid phase to the gas phase;

VI) running the liquid phase that remains after the expansion in step V) through an indirectly heated reaction zone, forming a hydrogen chloride- and phosgene-containing gas phase (generally also still containing proportions of evaporated solvent) which is removed, and an isocyanate- and solvent-containing liquid phase remaining which is withdrawn from the indirectly heated reaction zone;

VII) working up the isocyanate- and solvent-containing liquid phase obtained in step VI) to recover the solvent and obtain the isocyanate;

wherein in step V) the liquid phase withdrawn from the separation zone from step IV) is expanded by (i) first expanding this liquid phase in a first gas-liquid separation vessel, forming a first liquid phase and a first gas phase, (ii) then subsequently further expanding the first liquid phase in a second gas-liquid separation vessel, forming a second liquid phase and a second gas phase, (iii) then subsequently optionally further expanding the first liquid phase in a third gas-liquid separation vessel, forming a third liquid phase and a third gas phase, wherein the liquid phase run through the indirectly heated reaction zone in step VI) is the second (if step (iii) is not included) or (if step (iii) is included) the third liquid phase.

DETAILED DESCRIPTION

According to the invention, the gas phase that forms in the separation zone is "under a pressure in the range from 8.0 bar$_{(abs.)}$ to 50.0 bar$_{(abs.)}$, especially in the range from 15.0 bar$_{(abs.)}$ to 30.0 bar$_{(abs.)}$". The chemical conversions that proceed in the reaction zone form an (at least) hydrogen chloride- and phosgene-containing gas phase from the liquid reaction mixture obtained in step (III). The pressure values mentioned are thus based on the gas space of the separation zone. Here and hereinafter, all pressures should be understood as absolute pressures (identified as "bar$_{(abs.)}$").

Since the separation zone is "downstream in flow direction" of the reaction zone, which, in the terminology of the present invention, also means an open connection between the two zones for flow purposes, and since, moreover, the reaction zone and separation zone "are not heated and not cooled" (=adiabatic reaction regime), a temperature which, for a given temperature of the reaction mixture from step (III), is determined essentially—apart from heat losses resulting from imperfect insulation of the apparatuses used—by the enthalpies of reaction of the chemical processes that proceed (which are elucidated in detail further down) is established at every point in the reaction zone and separation zone. The pressure that is established is also determined firstly by the chemical processes that proceed. Preferably, however, a pressure-retaining valve for the gas phase that forms and a closed-loop liquid level controller for the liquid phase are provided in the separation zone, in order to be able to reliably ensure that pressure is within the abovementioned range—8.0 bar$_{(abs.)}$ to 50.0 bar$_{(abs.)}$, especially in the range from 15.0 bar$_{(abs.)}$ to 30.0 bar$_{(abs.)}$. Thus, however, the temperature in step IV) depends ultimately on the temperature of the reaction mixture to be fed to this step.

According to the invention, phosgene, based on the amino groups of the primary amine, is used in a "stoichiometric excess". In theoretical terms, 1 mol of phosgene reacts with 1 mol of primary amino groups (1 R—NH$_2$+1 COCl$_2$→1 R—NCO+2 HCl). An excess of phosgene of x % over primary amino groups therefore corresponds to a molar ratio n(phosgene)/n(–NH$_2$) (n=molar amount) of $$\frac{1+\frac{x}{100}}{1},$$

i.e., for example, $$\frac{1+\frac{40}{100}}{1}=1.40$$

with a 40% excess of phosgene or for example $$\frac{1+\frac{120}{100}}{1}=2.2$$

with a 120% excess of phosgene.

There follows firstly a brief summary of various possible embodiments of the invention:

In a first embodiment of the invention, which can be combined with all other embodiments, the solution of the primary amine provided in step I) has a proportion by mass of primary amine based on the total mass of this solution in the range from 25% to 50%, especially in the range from 30% to 45%, and the solution of phosgene provided in step II) has a proportion by mass of phosgene based on the total mass of this solution in the range from 45% to 90%, especially in the range from 55% to 80%.

In a second embodiment of the invention, which can be combined with all other embodiments, the mixing unit from step III) is not heated and not cooled.

In a third embodiment of the invention, which can be combined with all other embodiments, the mixing unit used in step III) comprises one or more dynamic mixers and especially does not comprise any static mixer.

In a fourth embodiment of the invention, which can be combined with all other embodiments, the reaction zone and separation zone from step IV) are disposed in a common reactor.

In a fifth embodiment of the invention, which is a particular configuration of the fourth embodiment, the reactor used is a tubular reactor in an upright arrangement.

In a sixth embodiment of the invention, which in a particular configuration of the fifth embodiment, the reaction mixture obtained in step III) flows through the reactor from the bottom upward.

In a seventh embodiment of the invention, which can be combined with all other embodiments, the indirectly heated reaction zone from step VI) is part of a shell and tube reactor, the liquid phase remaining after the expansion in step V) is run through the tube interior thereof and a heating medium is run through the tube exterior thereof, or the liquid phase remaining after the expansion in step V) is run through the tube exterior thereof and a heating medium is run through the tube interior thereof.

In an eighth embodiment of the invention, which can be combined with all other embodiments, the indirectly heated reaction zone from step VI) is part of a shell and tube reactor, the expanding in step V) comprises stages (i) and (ii) only, where the expanding is conducted in such a way that the first gas phase is obtained under a pressure in the range from 10 $bar_{(abs.)}$ to 20 $bar_{(abs.)}$, especially 12 $bar_{(abs.)}$ to 17 $bar_{(abs.)}$, and the second gas phase is obtained under a pressure in the range from 1.0 $bar_{(abs.)}$ to 5.0 $bar_{(abs.)}$, especially 2.0 $bar_{(abs.)}$ to 3.0 $bar_{(abs.)}$.

In a ninth embodiment of the invention, which can be combined with all embodiments that are not limited to two expansion stages, the expanding in step V) comprises stages (i), (ii) and (iii), where the expanding is conducted in such a way that the first gas phase is obtained under a pressure in the range from 15 $bar_{(abs.)}$ to 20 $bar_{(abs.)}$, especially 17 $bar_{(abs.)}$ to 18 $bar_{(abs.)}$, and the second gas phase is obtained under a pressure in the range from 5.0 $bar_{(abs.)}$ to 10 $bar_{(abs.)}$, especially 7.0 $bar_{(abs.)}$ to 8.0 $bar_{(abs.)}$, and the third gas phase is obtained under a pressure in the range from 1.0 $bar_{(abs.)}$ to 5.0 $bar_{(abs.)}$, especially 2.0 $bar_{(abs.)}$ to 3.0 $bar_{(abs.)}$.

In a tenth embodiment of the invention, which can be combined with all other embodiments, the gas phases obtained in steps IV), V) and VI) are worked up to obtain hydrogen chloride and phosgene and optionally solvent.

In an eleventh embodiment of the invention, which is a particular configuration of the tenth embodiment, the gas phases obtained in steps IV), V) and VI), prior to the workup, are adjusted to a common pressure and combined.

In a twelfth embodiment of the invention, which is a particular configuration of the eleventh embodiment, the gas phase obtained in step IV), the second gas phase obtained in step V) and any third gas phase obtained in this step, and the gas phase obtained in step VI) are adjusted to the pressure of the first gas phase obtained in step V).

In a thirteenth embodiment of the invention, which is a particular configuration of the twelfth embodiment, the combined gas phases are condensed and compressed and distilled for separation of hydrogen chloride and phosgene.

In a fourteenth embodiment of the invention, which can be combined with all other embodiments,
(i) methylene diphenylene diisocyanate and/or polymethylene polyphenylene polyisocyanate is prepared by reacting methylene diphenylene diamine and/or polymethylene polyphenylene polyamine with phosgene or
(ii) tolylene diisocyanate is prepared by reacting tolylenediamine with phosgene.

The embodiments briefly outlined above and further possible configurations of the invention are elucidated in detail hereinafter. Various embodiments are combinable with one another as desired unless the opposite is unequivocally apparent to the person skilled in the art from the context.

Step I) of the present invention, the providing of the amine solution required for the phosgenation, can be effected by any methods known from the prior art. The amine to be used is determined by the isocyanate desired. The process of the invention is suitable in principle for preparation of any desired aromatic, aliphatic and araliphatic isocyanates. Preference is given to using the process according to the invention for preparing methylene diphenylene diisocyanate (from methylene diphenylene diamine), polymethylene polyphenylene polyisocyanate (from polymethylene polyphenylene polyamine), mixtures of methylene diphenylene diisocyanate and polymethylene polyphenylene polyisocyanate (these mixtures are also referred to henceforth as MDI and the starting amine mixtures as MDA), tolylene diisocyanate (from tolylenediamine), xylylene diisocyanate (from xylylenediamine), pentane 1,5-diisocyanate (from pentane-1,5-diamine), hexamethylene diisocyanate (from hexamethylenediamine), isophorone diisocyanate (from isophoronediamine) and naphthyl diisocyanate (from naphthyldiamine), more preferably methylene diphenylene diisocyanate, mixtures of methylene diphenylene diisocyanate and polymethylene polyphenylene polyisocyanate, and tolylene diisocyanate. The process according to the invention is most preferably suitable for preparation of methylene diphenylene diisocyanate and mixtures of methylene diphenylene diisocyanate and polymethylene polyphenylene polyisocyanate. Methylene diphenylene diisocyanate is also referred to as diamine of the diphenylmethane series. Polymethylene polyphenylene polyisocyanate is also referred to as polyamine of the diphenylmethane series.

Processes for preparing the amines mentioned are known to those skilled in the art and therefore do not need any further elucidation at this point.

In step I), the amine to be phosgenated is dissolved in a solvent. This can be accomplished by means of mixing units known to the person skilled in the art, such as, more particularly, mixing tubes with static mixers as internals (frequently also referred to as static mixers for short). Suitable solvents usable in accordance with the invention are solvents that are inert under the reaction conditions, for example monochlorobenzene, dichlorobenzene (especially the ortho isomer), dioxane, toluene, xylene, methylene chloride, perchloroethylene, trichlorofluoromethane or butyl acetate. The solvent is preferably essentially free of isocyanate (target proportion by mass <100 ppm) and essentially free of phosgene (target proportion by mass <100 ppm), and this should be noted when using recycling streams. Preference is therefore given to working by a process as described in EP 1 854 783 A2. The solvents can be used individually or in the form of any desired mixtures of the solvents mentioned by way of example. Preference is given to using monochlorobenzene (MCB) or ortho-dichlorobenzene (oDCB), most preferably monochlorobenzene (MCB).

A preferred temperature of the resulting amine solution is in the range from 30° C. to 130° C., especially in the range from 60° C. to 100° C. This can in principle be achieved by appropriate control of the temperature of the amine and solvent starting materials, taking account of the enthalpy of dissolution. However, what is preferred in accordance with the invention, especially in addition to said control of the temperature of the starting materials, is provision of a heat exchanger downstream of the mixing of amine and solvent, which enables the exact adjustment of the amine solution to the desired temperature in the range from 30° C. to 130° C., especially in the range from 60° C. to 100° C., which is thus able to heat or cool according to the temperature immediately downstream of the mixing of the starting materials. Heat exchangers known to those skilled in the art are suitable for this purpose, such as, in particular, shell and tube heat exchangers and plate heat exchangers.

With regard to the amine concentration in the solution provided in step I), it is preferable to adjust the proportion by mass of primary amine based on the total mass of this solution to a value in the range from 25% to 50%, especially in the range from 30% to 45%.

Step II) of the present invention, the providing of the phosgene solution required for the phosgenation, can likewise be effected by any methods known from the prior art. Suitable mixing units and solvents are the same as described above for the primary amine. More particularly, it is preferable to dissolve the primary amine in step I) and phosgene in step II) in the same solvent in each case, i.e. most preferably in MCB. Processes for preparing phosgene are known to those skilled in the art and therefore do not need any further elucidation at this point.

A preferred temperature of the resulting phosgene solution is in the range from −20° C. to 120° C., especially in the range from −10° C. to 30° C. This can in principle be achieved by appropriate control of the temperature of the phosgene and solvent starting materials, taking account of the enthalpy of dissolution. However, what is preferred in accordance with the invention, especially in addition to said control of the temperature of the starting materials, is provision of a heat exchanger downstream of the mixing of phosgene and solvent, which enables the exact adjustment of the phosgene solution to the desired temperature in the range from −20° C. to 120° C., especially in the range from −10° C. to 30° C., which is thus able to heat or cool according to the temperature immediately downstream of the mixing of the starting materials. For this purpose, suitable heat exchangers are the same as described above for the primary amine.

With regard to the phosgene concentration in the solution provided in step II), it is preferable to adjust the proportion by mass of phosgene based on the total mass of this solution to a value in the range from 45% to 90%, especially in the range from 55% to 80%.

In step III) of the process according to the invention, the solution of the primary amine provided in step I) and the solution provided in step II) are mixed. Suitable mixing units for this purpose are those known to the person skilled in the art, such as static or dynamic mixers. Static mixers are characterized by the absence of moving parts; particular mention should be made here of mixing tubes with static mixers as internals (frequently also referred to as static mixers for short) or nozzles. By contrast, dynamic mixers contain moving parts, for example stirrer units. Particular mention should also be made here of the rotor-stator systems known from EP 0 830 894 A1 and EP 2 077 150 A1. Dynamic mixers, especially those of the rotor-stator type, are preferred for use in the present invention.

Preferably, the mixing unit from step III) is not heated and not cooled, meaning that the temperature of the reaction mixture obtained is determined solely by the enthalpy of mixing and the enthalpy of the reactions that have already set in the mixing unit. A transport conduit for the reaction mixture between the exit from the mixing unit from step (III) and the entrance into the reaction zone from step (IV) is preferably likewise neither heated nor cooled, but is preferably thermally insulated.

According to the invention, in the mixing in step III), a stoichiometric excess of phosgene based on the amino groups of the primary amine in the range from 40% to 200% of theory, preferably in the range from 40% to 120% of theory, more preferably in the range from 50% to 100% of theory, most preferably in the range from 50% to 75% of theory, is observed.

In step IV) of the process according to the invention, the first main part of the reaction to give the isocyanate takes place, under adiabatic conditions. What this means is that the reaction mixture that passes through step IV) is neither heated nor cooled during the reaction. The apparatuses used are insulated against heat losses, such that the evolution of temperature is determined by the enthalpy of reaction of the reactions that proceed.

Without wishing to be tied to a theory, it can be assumed that several reactions run in parallel in step IV). The primary amine reacts with phosgene to give the known carbamoyl chloride intermediate (exothermic reaction). The hydrogen chloride released here reacts with as yet unconverted amine to give amine hydrochloride (exothermic reaction), which dissolves in the solvent used (endothermic reaction). The cleavage of the carbamoyl chloride to give the desired isocyanate and hydrogen chloride also already takes place in part in step IV) (endothermic reaction). The change in temperature depends on the interplay of all these reactions. In general, in step IV), only a small change in temperature is observed, which suggests that there is a "balance" of exo- and endothermic reactions. In any case, the reactions in step IV) form a gas phase, which is separated from the remaining liquid phase in the separation zone. Reaction zone and separation zone are preferably disposed in a common reactor. Suitable phosgenation reactors for this purpose are customary phosgenation reactors known to the person skilled in the art, such as in particular, tubular reactors in an upright arrangement (tube reactors; if the ratio of height to diameter is relatively small, reference is also made to tower reactors or reactor towers), through which the reaction mixture obtained in step III) preferably flows from the bottom upward. To narrow the dwell time distribution, the reactors in the reaction zone may be segmented by internals known to the person skilled in the art. In the upper part of the reactor, the gas phase formed and the remaining liquid phase are withdrawn separately. The phase separation takes place spontaneously.

In step V) of the process according to the invention, the liquid process product obtained in step IV) is expanded in two or three stages to a lower pressure, preferably to a pressure in the range from 1.0 $bar_{(abs.)}$ to 20 $bar_{(abs.)}$, measured in the gas phase obtained in the last stage. For this purpose, gas-liquid separation vessels (also referred to as gas separators) that are connected in series for the procedure according to the invention are used. This forms a gas phase containing hydrogen chloride and unconverted phosgene in each stage. In this multistage expansion, the liquid phase obtained after expansion of the first stage is the feedstock for the second stage and so forth.

In one embodiment of the invention, the expanding in step V) comprises stages (i) and (ii) only, where the expanding is conducted in such a way that the first gas phase is obtained under a pressure in the range from 10 $bar_{(abs.)}$ to 20 $bar_{(abs.)}$, especially 12 $bar_{(abs.)}$ to 17 $bar_{(abs.)}$, and the second gas phase is obtained under a pressure in the range from 1.0 $bar_{(abs.)}$ to 5.0 $bar_{(abs.)}$, especially 2.0 $bar_{(abs.)}$ to 3.0 $bar_{(abs.)}$.

In a further embodiment of the invention, the expanding in step V) comprises stages (i), (ii) and (iii), where the expanding is conducted in such a way that the first gas phase is obtained under a pressure in the range from 15 $bar_{(abs.)}$ to 20 $bar_{(abs.)}$, especially 17 $bar_{(abs.)}$ to 18 $bar_{(abs.)}$, and the second gas phase is obtained under a pressure in the range from 5.0 $bar_{(abs.)}$ to 10 $bar_{(abs.)}$, especially 7.0 $bar_{(abs.)}$ to 8.0 $bar_{(abs.)}$, and the third gas phase is obtained under a pressure in the range from 1.0 $bar_{(abs.)}$ to 5.0 $bar_{(abs.)}$, especially 2.0 $bar_{(abs.)}$ to 3.0 $bar_{(abs.)}$.

In each of these embodiments, it is preferable to dispose the gas-liquid separation vessel intended for the last expansion and the indirectly heated reaction zone from step VI) in a common apparatus. One example of a possible configuration is described below.

In step VI), the liquid phase remaining after the last expansion stage in step IV) is converted further in an indirectly heated reaction zone to form a hydrogen chloride- and phosgene-containing gas phase ("isothermal process regime"). This can take place in heatable reactors known to the person skilled in the art. Especially suitable for this purpose are shell and tube reactors (in a vertical arrangement). The liquid phase from step IV) can be run here through the interior of the tubes of the shell and tube reactor (tube interior) or through the space between the tubes of the shell and tube reactor which is bounded on the outside by the reactor wall that encases the bundle of tubes (tube exterior). The heating medium—a heat carrier oil, a salt melt, steam or the like—is then run through the respective other space, such that it does not come into physical contact with the liquid process product to be converted (indirect heating). The liquid phase from the last expansion stage from step IV) here runs through the shell and tube reactor in a vertical arrangement preferably from the top downward. In the preferred configuration of the invention with integration of the gas-liquid separation vessel envisaged for the last expansion stage of step IV) into the apparatus from step V) containing the indirectly heated reaction zone, the gas-liquid phase separation then takes place in a dome at the top of the shell and tube reactor.

In steps IV), V) and VI), gas phases containing hydrogen chloride and phosgene, with or without solvent, are obtained. These gas phases are preferably worked up to recover products of value. The workup especially serves for the separation of phosgene and hydrogen chloride from one another and from impurities, and can be effected, for example, by absorption of the phosgene in a solvent or by distillative separation after compression and liquefaction. The hydrogen chloride gas obtained is suitable for further oxidation to chlorine, which is required for the preparation of the phosgene required for step II). The oxidation can be effected electrolytically or catalytically with oxygen (called the Deacon process). Recovered phosgene, optionally containing solvent, can be used in step II).

In each case, it is appropriate to adjust the gas phases obtained in steps IV), V) and VI) prior to the workup to a common pressure and combine them.

In principle, this can be done by expanding all gas phases to the lowest pressure (i.e. to the pressure of the gas phase obtained in step VI)) or an even lower pressure and then purifying them further. This procedure is preferred especially in the case of workup by absorption.

However, the fact that, in the process according to the invention, a majority of the hydrogen chloride- and phosgene-containing gas phases is obtained at comparatively high pressure opens up advantages especially in the purification by distillation. Preference is given here to a procedure in which the second gas phase obtained in step VI) and any third gas phase obtained are adjusted by compression to the pressure of the first gas phase, and the first, second and any third gas phase are subsequently combined with one another and, after appropriate pressure adjustment, with the gas phases from step IV) and step VI). The gas phase obtained in step IV) is expanded here to the pressure of the first gas phase of step V). The gas phase obtained in step VI) is under a lower pressure than the first gas phase from step V) and is compressed to that pressure. If step V), by contrast, is conducted in one stage, the entire gas phase formed in the expansion is obtained at a relatively low pressure (namely at a pressure corresponding to the pressure of the gas phase obtained in the last expansion stage of the process according to the invention) and must consequently also be compressed in its entirety. Overall, in the procedure according to the invention, the volume of the gas streams to be compressed is comparatively small, which, by comparison with a single-stage expansion, enables the option of using smaller compressors, which reduces capital costs and maintenance expenditure. The adjustment of all gas phases to the (comparatively high) pressure of the first gas phase from step V) (rather than to the lower pressure of, for example, the last gas phase from step V) or the gas phase from step VI)) simplifies the condensation of the combined gas phases in the further workup, which is required to distillatively separate hydrogen chloride and phosgene. In this embodiment, therefore, the purification of the gas phases adjusted to the common pressure is preferably followed by liquefaction thereof by condensation and compression and subsequent distillation. This distillation affords cleaned hydrogen chloride gas as top product and liquid phosgene (or a phosgene-solvent mixture) as bottom product, which can be recycled into the process. The combination of the process according to the invention with the catalytic oxidation of the hydrogen chloride with oxygen—a process that makes comparatively high demands on the purity of the reactants—is particularly advantageous since, in the process according to the invention, a majority of the hydrogen chloride- and phosgene-containing gas phases is obtained at comparatively high pressure in a manner inherent to the process, and this, as mentioned above, facilitates the compression required for distillative purification. Moreover, it becomes economically viable to conduct the distillation of the phosgene-hydrogen chloride mixture at comparatively high pressure, which is advantageous for a Deacon process in which the hydrogen chloride supplied is under elevated pressure.

The process according to the invention results at least in the following advantages without impairing product quality with regard to secondary component formation, colour, acidity, NCO content and iron content:

i) avoidance of foaming of the reaction solution in the pressure-lowering step; hence assurance of a stable mode of operation;

ii) utilization of the higher gas pressure for a subsequent distillative separation of the phosgene-HCl gas mixture for reuse of the phosgene in step II) and production of a phosgene-free HCl gas for further obtaining of $Cl_2$ gas (feedstock for preparation of phosgene);

iii) possibility of using smaller compressors, hence reduced capital costs and maintenance expenditure and reduced space demands.

The invention is elucidated in detail hereinafter by examples.

EXAMPLES

Example 1 (Inventive): Computer Simulation of the Process According to the Invention for Production on the Industrial Scale, Two-Stage Expansion In an MDI plant, 40.0 t/h of MDA at a temperature of 130° C. are mixed with 94.5 t/h of MCB at a temperature of 52° C. as solvent by means of a static mixer to give a 30.0% MDA solution (step I)). Phosgene is mixed with MCB in a phosgene dissolution tank to obtain a 60.0% phosgene solution (step II)). 106.7 tonnes per hour of this phosgene solution at a temperature of 3.0° C. are run through a heat exchanger and thus cooled down to a temperature of −1° C. In an analogous manner, 134.5 tonnes per hour of the 30% MDA solution at a temperature of 80.0° C. are run through a heat exchanger and thus cooled down to a temperature of 60° C. The MDA and phosgene solutions having temperatures thus adjusted are run into a dynamic mixer (step III)). The temperature at the exit of the dynamic mixer is adjusted to 130° C.

The liquid reaction mixture leaving the mixer is run under adiabatic conditions through a phosgenation reactor (tower reactor) insulated against heat losses (step IV)). The pressure at the exit from the phosgenation reactor is adjusted by means of a pressure-retaining valve to 22 $bar_{(abs.)}$; the exit temperature is 120° C. The dwell time of the phosgenation reaction from the mixer to the exit from the phosgenation reactor is 5 min. At the top of the tower reactor, an HCl- and phosgene-containing gas phase (also still containing fractions of evaporated MCB) separates out. The reaction solution withdrawn from the reactor is expanded in two stages, each in a gas separator, to first 15 $bar_{(abs.)}$ and then to 3 $bar_{(abs.)}$ (step V)) and then converted further in a heated reactor at 130° C. and 3 $bar_{(abs.)}$ (step VI)).

Subsequently, the reaction solution leaving the heated reactor is worked up with recycling of the solvent to obtain the isocyanate (step VII)). The workup comprises a dephosgenation and removal of solvent. In the distillation for removal of solvent, the bottom product obtained is 50.0 t/h of MDI, which is separated by means of further distillation steps into methylene diphenylene diisocyanate and a mixture of methylene diphenylene diisocyanate and polymethylene polyphenylene polyisocyanate.

In a real production plant, the flow rates mentioned here can advantageously be implemented in multiple reaction lines operated in parallel.

The invention claimed is:

1. A process for preparing an isocyanate by reacting a primary amine with phosgene, comprising:
   I) providing a solution of the primary amine in a solvent;
   II) providing a solution of phosgene in a solvent;
   III) mixing the solution of the primary amine in a solvent and the solution of phosgene in a solvent to give a liquid reaction mixture having a temperature of 110° C. to 145° C. and a stoichiometric excess of phosgene, based on the amino groups of the primary amine, of 40% to 200% of theory;
   IV) running the liquid reaction mixture through a reaction zone and a separation zone arranged downstream in flow direction of the reaction zone to form a gas phase having a pressure of 8.0 $bar_{(abs.)}$ to 50.0 $bar_{(abs.)}$, where the reaction zone and the separation zone are not heated and not cooled, and where remaining liquid phase and the gas phase are removed from the separation zone separately from one another;
   V) expanding the liquid phase withdrawn from the separation zone to thereby partially convert the liquid phase to the gas phase;
   VI) running liquid phase that remains after the expansion through an indirectly heated reaction zone, forming a hydrogen chloride- and phosgene-containing gas phase which is removed, and an isocyanate- and solvent-containing liquid phase remaining which is withdrawn from the indirectly heated reaction zone; and
   VII) working up the isocyanate- and solvent-containing liquid phase to recover the solvent and obtain the isocyanate;
   wherein: in step V) the liquid phase withdrawn from the separation zone is expanded by an at least two-stage expansion process comprising:
   (i) a first stage of expanding the liquid phase withdrawn from the separation zone in a first gas-liquid separation vessel to form a first liquid phase and a first gas phase, and
   (ii) a second stage of further expanding the first liquid phase in a second gas-liquid separation vessel to form a second liquid phase and a second gas phase,
   wherein the liquid phase that remains after the expansion is the liquid phase obtained in the last stage of the expansion process.

2. The process of claim 1, in which the solution of the primary amine in a solvent has a proportion by mass of primary amine of 25% to 50%, based on the total mass of the solution of the primary amine in a solvent, and the solution of phosgene in a solvent has a proportion by mass of phosgene of 45% to 90%, based on the total mass of the solution of phosgene in a solvent.

3. The process of claim 1, in which the mixing of the solution of the primary amine in a solvent and the solution of phosgene in a solvent is carried out in a mixing unit that is not heated and not cooled.

4. The process of claim 1, in which in which the mixing of the solution of the primary amine in a solvent and the solution of phosgene in a solvent is carried out in a mixing unit comprising one or more dynamic mixers.

5. The process of claim 1, in which the reaction zone and the separation zone are disposed in a common reactor.

6. The process of claim 5, in which the reactor is a tubular reactor in an upright arrangement.

7. The process of claim 6, in which the reaction mixture flows upwardly through the reactor.

8. The process of claim 1, in which the indirectly heated reaction zone is a part of a shell and tube reactor, wherein the liquid phase remaining after the expansion passes through the tube interior thereof and a heating medium passes through the tube exterior thereof, or wherein the liquid phase remaining after the expansion passes through the tube exterior thereof and a heating medium passes through the tube interior thereof.

9. The process of claim 1, in which the expanding comprises stages (i) and (ii) only, where the expanding is conducted in such a way that the first gas phase is obtained under a pressure of 10 $bar_{(abs.)}$ to 20 $bar_{(abs.)}$, and the second gas phase is obtained under a pressure of 1.0 $bar_{(abs.)}$ to 5.0 $bar_{(abs.)}$.

10. The process of claim 1, in which the gas phases obtained in steps IV), V) and VI) are worked up to obtain hydrogen chloride and phosgene and optionally solvent.

11. The process of claim 10, in which the gas phases obtained in steps IV), V) and VI), prior to the workup, are adjusted to a common pressure and combined.

12. The process of claim 11, in which the gas phase obtained in step IV), the second gas phase obtained in step V) and any third gas phase obtained, and the gas phase obtained in step VI) are adjusted to the pressure of the first gas phase obtained in step V).

13. The process of claim 12, in which the combined gas phases are condensed and compressed and distilled for separation of hydrogen chloride and phosgene.

14. The process of claim 1, in which
(i) methylene diphenylene diisocyanate and/or polymethylene polyphenylene polyisocyanate is prepared by reacting methylene diphenylene diamine and/or polymethylene polyphenylene polyamine with phosgene or
(ii) tolylene diisocyanate is prepared by reacting tolylenediamine with phosgene.

15. The process of claim 1, wherein expanding further comprises:
(iii) in a third stage, further expanding the second liquid phase in a third gas-liquid separation vessel, forming a third liquid phase and a third gas phase.

16. The process of claim 15, where the expanding is conducted in such a way that the first gas phase is obtained under a pressure of 15 $bar_{(abs.)}$ to 20 $bar_{(abs.)}$, and the second gas phase is obtained under a pressure of 5.0 $bar_{(abs.)}$ to 10 $bar_{(abs.)}$, and the third gas phase is obtained under a pressure of 1.0 $bar_{(abs.)}$ to 5.0 $bar_{(abs.)}$.

* * * * *